United States Patent [19]
Luckman et al.

[11] Patent Number: 5,152,797
[45] Date of Patent: Oct. 6, 1992

[54] MODULAR PROSTHESIS

[75] Inventors: Thomas Luckman, E. Falmouth; Keith W. Greer, S. Easton; Kenneth G. Arsenault, Ware, all of Mass.

[73] Assignee: Johnson & Johnson Orthopaedics, Inc., Raynham, Mass.

[21] Appl. No.: 782,702

[22] Filed: Oct. 25, 1991

[51] Int. Cl.⁵ .......................... A61F 2/38; A61F 2/30; A61F 2/40; A61F 2/36
[52] U.S. Cl. ...................................... 623/20; 623/16; 623/19; 623/23; 623/18
[58] Field of Search ............................. 623/16, 18–23

[56] References Cited

U.S. PATENT DOCUMENTS

| | | | |
|---|---|---|---|
| 4,298,992 | 11/1981 | Burstein et al. | 623/20 |
| 4,936,847 | 6/1990 | Manginelli | 623/20 |
| 4,944,757 | 2/1990 | Martinez et al. | 623/20 |
| 4,995,883 | 2/1991 | Demane et al. | 623/23 |
| 5,019,103 | 5/1991 | Van Zile et al. | 623/20 |
| 5,047,058 | 9/1991 | Roberts et al. | 623/20 |

Primary Examiner—Ronald Frinks
Attorney, Agent, or Firm—Michael O. Tatlow

[57] ABSTRACT

A modular prosthesis system having generally planar bone contact surface with an undercut edge around the periphery of the surface and includes augmentation devices which can be attached to the planar surface with a cam locking mechanism secured to the undercut edge to increase the thickness of the prosthesis.

9 Claims, 5 Drawing Sheets

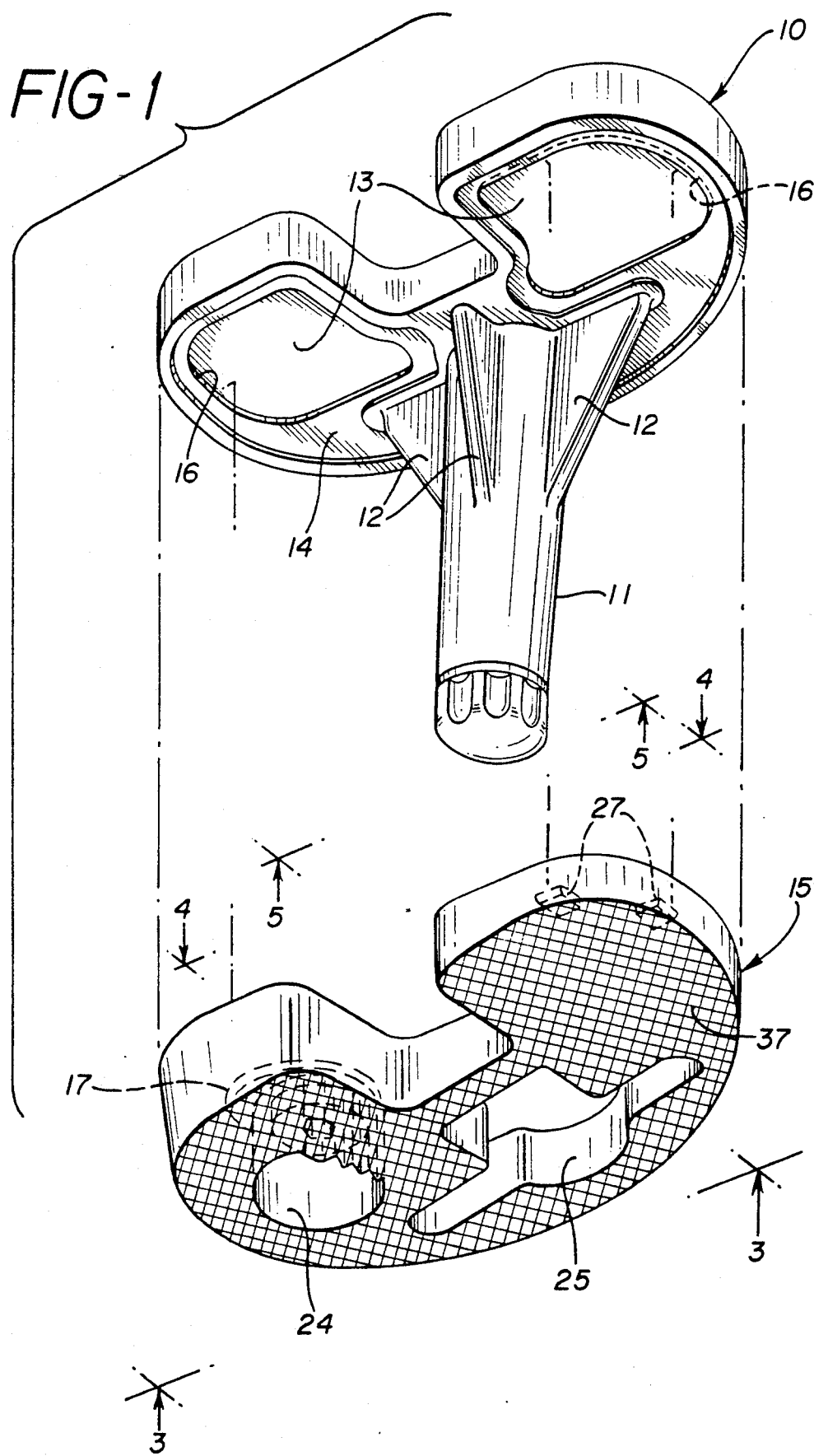

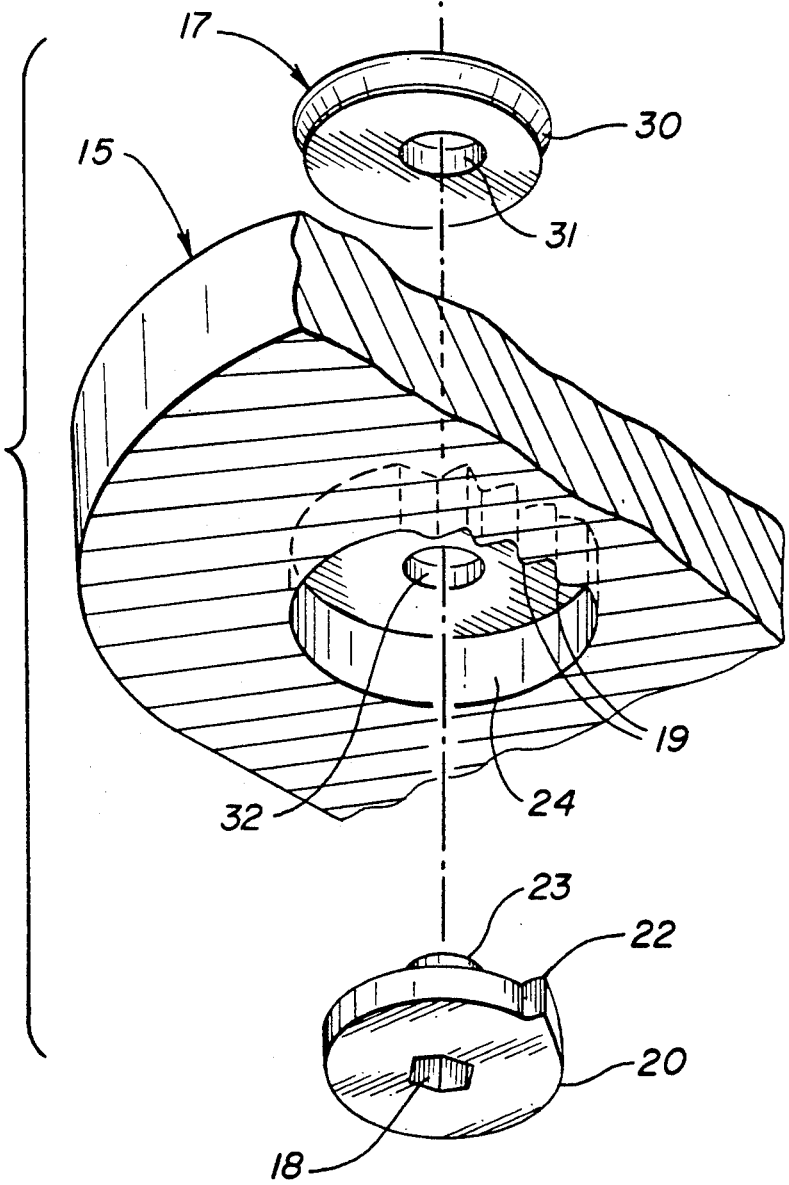

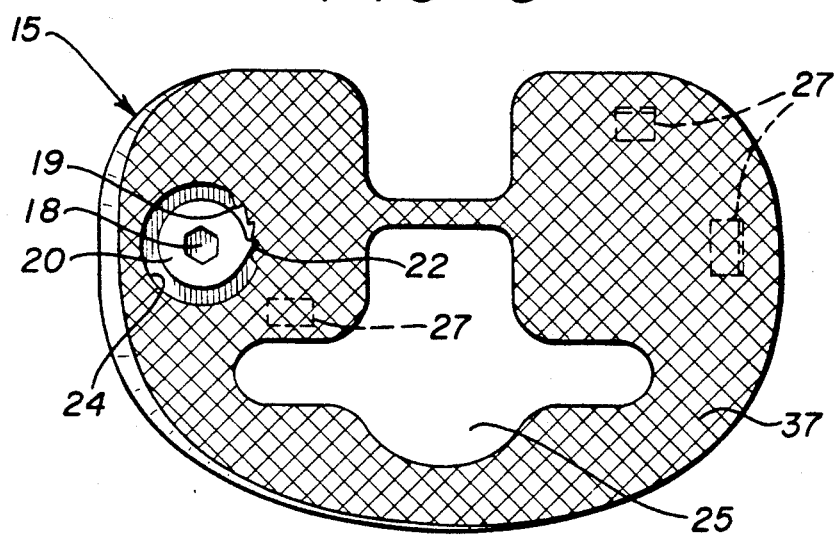
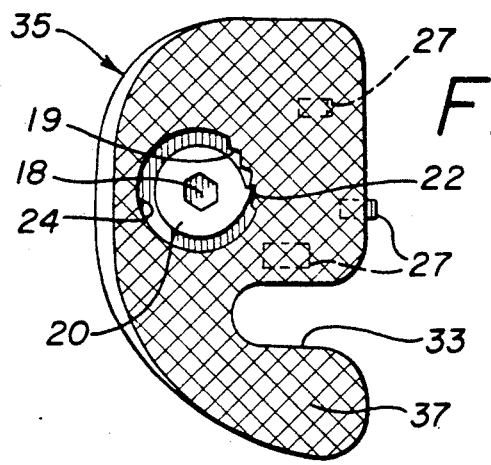
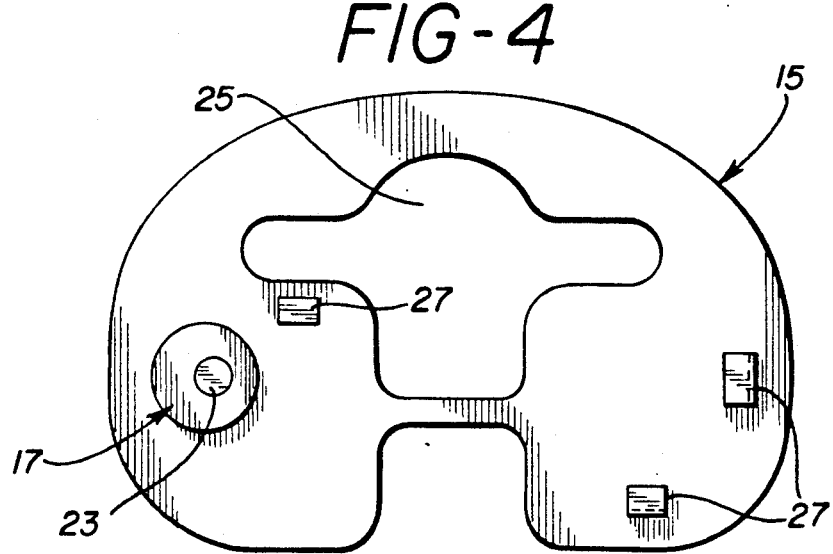

MODULAR PROSTHESIS

The present invention relates to a joint prosthesis system and more particularly, to a prosthesis in which the bone contact surfaces can be adjusted or augmented by the addition of modular components to adjust the thickness of the prosthesis in those areas where the implanted prosthesis will be in direct contact with the bone.

BACKGROUND OF THE INVENTION

The present invention relates to a system for the modification of a prosthesis so that the basic prosthesis can be used in normal surgical procedures and in which certain surfaces can also be adjusted to be used in revision knee surgery or in normal surgery when it is desired to augment the thickness of the prosthesis at various bone contact surfaces. For example, in the case of revision surgery, a previously implanted knee prosthesis may have failed for a number of different reasons. These reasons include a malpositioning of the prosthesis on original implantation, loosening of the prosthesis, infection, or dislocation. These categories are not necessarily exclusive because infection, for example, may cause a loosening of the prosthesis which in turn, may cause dislocation. In some instances, it is necessary to remove additional bone during revision surgery because of bone infection, or because of stems fractures or fatigue fractures of the prosthesis and resulting bone damage.

In addition to its use in revision prosthesis, the present prosthesis may also be used in the initial implantation surgery. On occasion, a surgical procedure cannot be carried out as planned because during the surgical procedure it is discovered that a particular area of bone is not adequate to support the prosthesis intended to be implanted. In the case of revision surgery or in situations where X-ray or other imaging indicates a problem with the bone, it is possible to custom make a prosthesis to fit a particular patient and overcome the problems of implantation. However, it would be preferable to have the capability of modifying a prosthesis during the surgical procedure in the event that untoward problems become evident during the surgical procedure.

Previously used procedures for modifying the bone contact surface of tibial components of a knee prosthesis include drilling holes in the prosthesis and attaching the augmentation component with bolts or screws or cementing the augmentation devices to the distal or bone contact side of the prosthesis.

U.S. Pat. No. 4,995,883 discloses a hip prosthesis with adjustment pads which may be used to increase the thickness of the prosthesis in selected areas. The pads are secured in position on the body of the prosthesis using bolts and/or expandable bushings.

SUMMARY OF INVENTION

The present invention provides a system which includes a prosthesis in which the surfaces of the prosthesis which are in direct contact with the bone can be augmented by augmentation devices to increase the dimensions of the basic prosthesis to compensate for areas of bone which are removed because of weakness in or damage to the bone structure of the patient.

The attachment system of the present invention does not employ bolts or screws which are difficult to secure by surgeons in the operating room but uses a simply operated and cam locking mechanism. The locking mechanism of the present invention is an integral part of the augmentation device which allows the augmentation device to readily affix to the prosthesis, without the necessity of positioning screws or bolts in the device in the operating room.

The system of the present invention can be used with different types of implantable prosthesis. The system is most effectively used with prosthesis which have a generally flat bone contact surface or a bone contact surface with minimum curvature. Implantable prosthesis having such flat surfaces include tibial components of knee prosthesis, femoral components of total hip prosthesis and shoulder prosthesis. The invention will hereafter be described in an augmentation device for a tibial component of a total knee prosthesis, but the locking mechanism can be used to secure augmentation devices in other prosthesis as mentioned above.

Augmentation devices of the system of the present invention can be readily fitted to the inferior or distal surface of the tibial component which is in contact with the bone so that damaged bone can be removed while still allowing the same basic prosthesis to be employed. The augmentation devices are furnished in various thicknesses and in various angular configurations so that a surgeon can determine the correct modification to any tibial prosthesis and augment the prostheses with the correct augmentation device to compensate for bone removal. The augmentation devices may also be provided to vary only a portion of the tibial prostheses. The augmentation devices can be readily and securely affixed to the distal portion of the prosthesis without changing the configuration of the proximal portion of the prosthesis. The tibial prosthesis usually employ an ultra high molecular weight polyethylene bearing surface on the proximal side of the tibial prosthesis. This bearing surface may be permanently bonded to the proximal portion of the tray portion of the tibial prosthesis or may be provided in the form of an insert which can be removably fitted into the tray. The metal bearing surfaces of the femoral component of the prosthesis are in contact with the polyethylene bearing surface of the tibial component when implanted.

DESCRIPTION OF THE DRAWINGS

FIG. 1 shows an exploded isometric view from the distal side of a tibial prosthesis showing the present invention.

FIG. 2 shows a fragmentary exploded view of the locking mechanism used to secure the augmentation devices of the present invention.

FIG. 3 shows a bottom plan view of a full width augmentation device of the present invention.

FIG. 3A shows a bottom plan view of a partial augmentation device of the present invention.

FIG. 4 shows a top plan view of a full width augmentation device of the present invention.

DETAILED DESCRIPTION OF THE INVENTION

Figure 5:
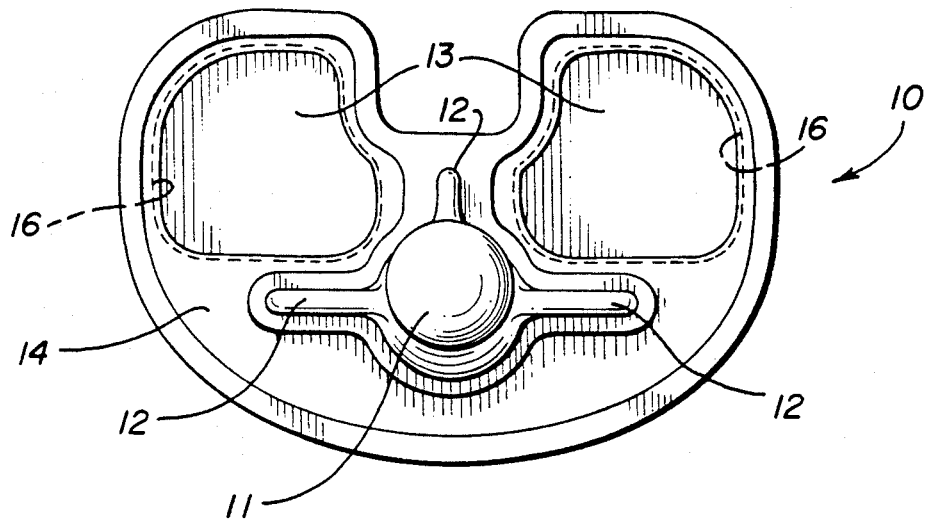
FIG. 5 shows a bottom plan view of a tibial prosthesis before the attachment of an augmentation device.
Figure 6:
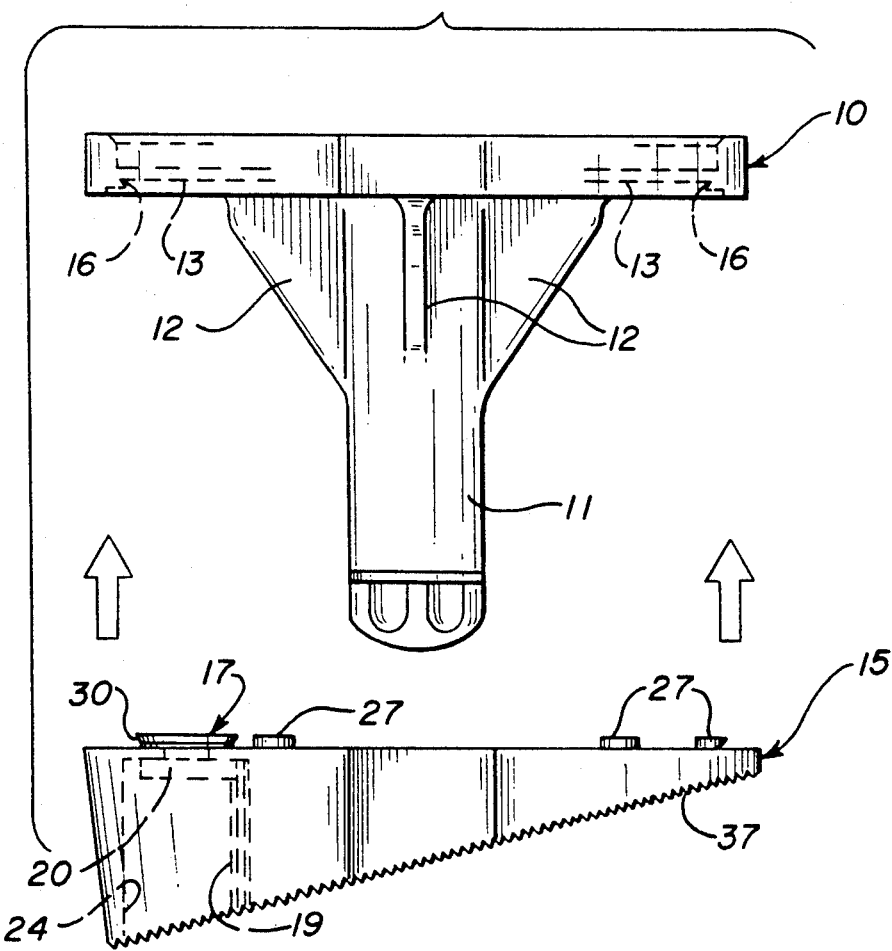
FIG. 6 shows side elevation in an exploded view of a tibial component and of the augmentation device of the present invention.
Figure 7:
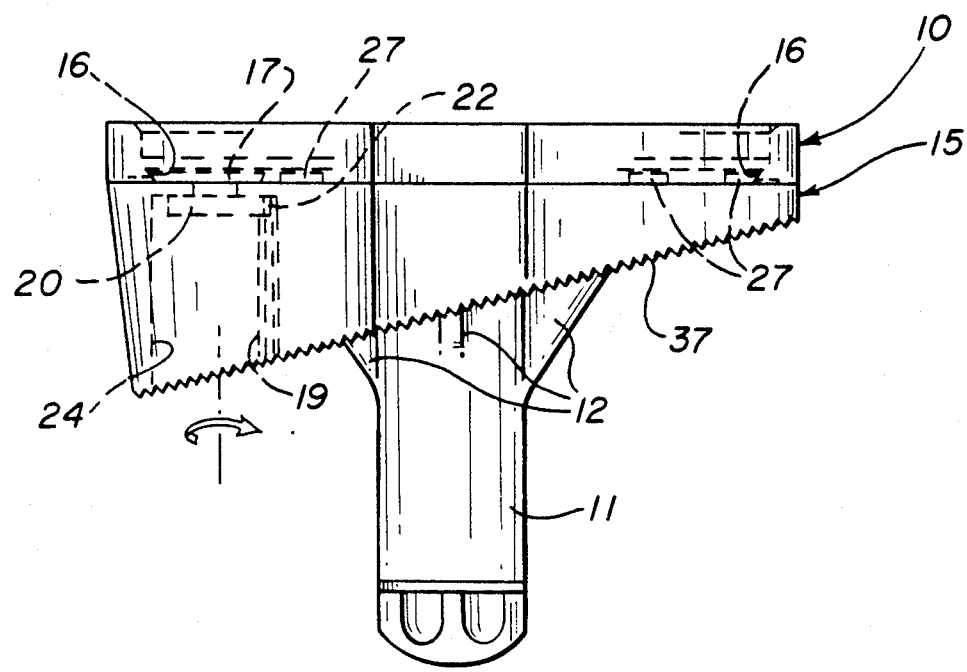
FIG. 7 is a side view of a tibial prosthesis with a augmentation device attached.

FIG. 1 shows an exploded isometric view from the distal side of the tibial prosthesis showing the distal portion of the prosthesis and the augmentation device of the present invention. The tibial prosthesis includes a metal tray or platform 10 which has a relatively flat surface on its proximal side. The flat surface or tibial tray is adapted to receive an ultra high molecular weight polyethylene insert bearing surface (not shown). This bearing surface may be of any particular design well know in the art, such as that shown in U.S. Pat. No. 4,298,992 the disclosure of which is incorporated herein by reference. The distal surface 14 of the tibial prosthesis has a stem 11 leading distally from its central area. The stem 11 has a number of triangular shaped keels 12 which are affixed in contact with the distal surface 14 of the tibial platform 10. The stem 11 and the keels 12 are provided to support the tibial prosthesis 10 in the tibia 20 of the patient. Upon implantation, bone is removed from the patient's tibia to provide an opening in the bone that will correspond generally to the configuration of the stem 11 and the keels 12. The stem and keel will then be implanted into the tibia with the use of the cement. The stem and keel may also be press fit after bone is removed in substantially the same shape as the stem and keel. In a press fit procedure, no cement is used, as the stem and keels of the prosthesis precisely fits into the opening cut into the bone. The lower or distal surface 14 of the tibial platform has a number of cement recesses 13, which, when the prosthesis is used without an augmentation device, allow bone cement to be placed in contact with the bone. There is a undercut portion 16 (best seen in FIG. 8) in the cement recesses which, as later explained, is used to secure the augmentation device to the distal surface of the tibial component.

The augmentation device 15 shown in FIG. 1 is a full width wedge which extends across the prosthesis from the lateral to the medial side of the prosthesis. Generally the periphery of the augmentation device will not extend beyond the periphery of the prosthesis to which it is secured. In the full width augmentation device shown in FIG. 1, the periphery of the augmentation device is coextensive with the periphery of the prosthesis to which it is secured which is preferred. The device has an opening 25 through which the stem 11 and the keels 12 can protrude. The particular shape of the opening is made to correspond to the particular configuration of the stem and any keel or other structural member that might be used to stabilized the tibial prosthesis in the tibia. The device shown in FIG. 1 is angular in that the thickness of the device varies from the lateral to the medial side and the proximal surface is at an angle to the distal surface. Augmentation devices of this type would be employed when the bone at the surface of the tibia would be trimmed at an angle to ensure that the remaining bone structure would be sufficiently strong to support the tibial platform. The distal surface of the device has the stem and keel opening 25 of a configuration to allow the device to pass over the stem and keels when the device is fitted to the prosthesis. There is also an opening or cavity 24 which is used to gain access to the pawl 20 affixed to the locking cam 17 employed to lock the tibial wedge to the distal side of the tibial prosthesis. This locking mechanism is shown in more detail in FIG. 2 and FIG. 8.

FIG. 3 shows the distal side of the augmentation device or the side of the device which will contact the bone. Shown in dotted lines in FIG. 3 are a number of lugs 27 which are positioned on the proximal surface of the wedge so that the lugs can engage the undercut portion 16 of the cement recess on the distal side of the tray. There are at least two pairs of locking mechanisms, i.e., two lugs or a lug and a locking cam to affix the augmentation device to a cement recess. The lugs are fitted into the cement recesses 13 when the augmentation wedge is fitted onto the distal side of the tibial prosthesis.

The cam mechanism shown in exploded view in FIG. 2 is used to lock the augmentation device to the distal side of the tibial tray. The cam locking mechanism includes a cam 17 which has a beveled surface 30 cut at an angle so that it will engage with angle on the undercut portion 16 of the cement recess. There is an opening 31 eccentrically positioned in the cam which will receive the shaft 23 which is mounted on the pawl 20. There is also an opening 32 in the augmentation device which is larger in diameter than the diameter of the shaft 23 to allow the shaft 23 to easily turn within the opening 32. There is a hex drive socket 18 cut into the bottom of the pawl 20 to turn the pawl. There are a number of teeth 19 which are cut into the side of the cavity 24 on the distal surface of the augmentation device which teeth will mesh with the tooth 22 on the pawl 20 to lock the cam 17 in position. The locking device shown in FIG. 2 can be assembled by placing the cam 17 on the upper surface of the wedge and positioning the pawl 20 so that the shaft extends through the opening 32 and into the opening 31 on the cam. The shaft is then electron beam welded to the cam or affixed to the cam in some other permanent fashion. Because the shaft of the pawl is set in the cam in an eccentric manner, as the cam is rotated a portion of the beveled edge 30 of the cam will eventually come into contact with the undercut portion 16 of the cement recess on the distal surface of the tibial tray and lock the cam into the tray. The interlocking of the tooth 22 on the pawl with the teeth 19 in the augmentation device will securely fix the augmentation device as the interlocking teeth will prevent the pawl from reverse rotation which could unlock the cam. There is a lug located on the proximal surface of the wedge in proximity to the cam to provide additional fixation in the cement recess.

Figure 8:
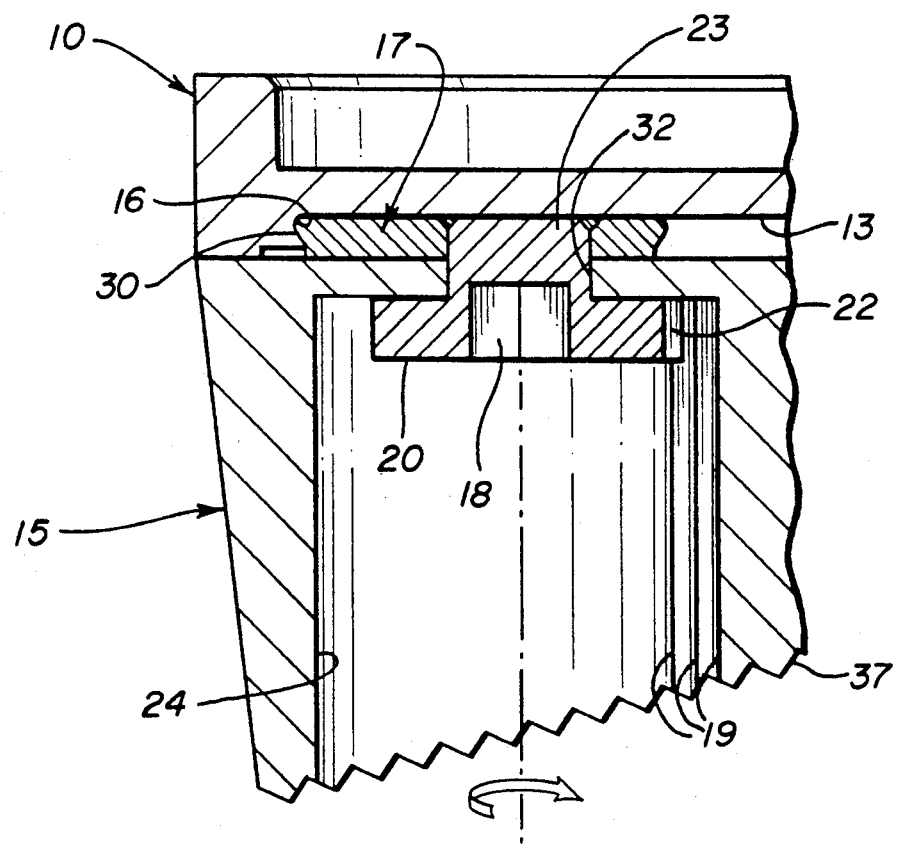
FIG. 8 is an enlarged view, in section, of the locking mechanism used in the present inventions.

The relationship between the pawl and the cement recess is best shown in FIG. 8 which shows the eccentric mounting and the cam fitted into the cement recess to lock the augmentation device 15 in position on the distal surface of the tibial component.

FIG. 3A shows an augmentation device which increases the thickness of only a portion of the width of the tibial component. The device 35 includes three lugs 27 which are positioned on the proximal surface of the device to engage one of the cement recesses 13 on the distal surface 14 of the tibial component. The cam and pawl are identical to that previously described. There is a slot 33 which is of adequate size to fit around the keel 12 of the tibial component.

When the device of the present invention is used, the surgeon would determine, either prior to the surgical procedure or during the surgical procedure, that additional bone on the tibial would have to be removed because the tibia bone would be in such diseased or damaged state that it would not be strong enough to support the tibial prosthesis. The surgeon would select a particular augmentation device which would fill in the space between the stabilized bone and the distal surface of the tibial tray. The surgeon would then secure the selected device in its position on the distal side of the tibial tray. The surgeon would place the lugs which are on one side of the full width or partial width wedges as shown in FIGS. 3 and 3A into the cement recess. The pawl 20 would then be turned until the cam 17 is securing locked in the cement recess. Turning the pawl less than a single revolution will be sufficient to lock the augmentation device to the prosthesis. The pawl 20 would then be turned to mesh the tooth on the pawl with the teeth 19 in the cavity 24 to affix the device onto the distal surface of the prosthesis. The surgical procedure will then proceed as normal.

It should be noted that the distal side or that side of the augmentation device which comes in contact with the bone can be made with a knurled or cut surface 37 to provide a greater capacity for receiving cement or for gripping the bone surface. It should be understood that the modular prosthesis system would be provided to the operating surgeon with augmentation devices of different thicknesses and with different angles between opposed surfaces, for example, at angles of 5°, 10°, 15° and 20° to the horizontal so that the proper device could be selected for the particular patient. This would be true for the full size devices shown in FIG. 3 or the partial wedges shown in FIG. 3A. In addition to devices cut with angular angles, augmentation devices made with constant thickness would be provided. These devices would be used in situations where a greater then usual amount of bone would have to be removed from the tibia. The ultra high molecular weight polyethylene bearing surfaces which are fitted on the proximal side of the tibial can only be of a limited height without risking severe cold flow. It may therefore be necessary to augment the total thickness of the tibial tray from the medial to the lateral side.

Although the devices shown in the drawings all extend from the medial to the lateral side of the tibial tray, it is also possible to employ wedges which extend from the anterior to the posterior side of the tibial tray.

The augmentation devices are preferably constructed of metal and most preferably of the same metal alloys as the basic prosthesis. Generally, these metals are stainless steel, chrome cobalt alloys or titanium alloys. If the augmentation device is constructed of a metal alloy which differs from the alloy used in the prosthesis, an isolation coating is applied between the surfaces of the prosthesis and the augmentation device that are in contact. This coating reduces the possibility of galvanic corrosion caused by the use of dissimilar alloys. The coating may be polyethylene, poly (methylmethacylate) or poly ethyl ether ketone or any other biocompatible coating composition.

The advantage of the present system is that the augmentation device can be readily secured to the prosthesis without the use of bolts or screws.

What we claim is:

1. A prosthesis system comprising a prosthesis having a at least one substantially planar surface, a recess in said planar surface said recess having an undercut edge adjacent at least a portion of its periphery, and an augmentation device adapted to increase a dimension of the prosthesis, said augmentation device having a proximal surface to contact the planar surface of the prosthesis and a distal surface opposite the proximal surface to contact the bone, a cam locking mechanism on the proximal side of the device to engage with the recess on said planar surface of the prosthesis to secure the augmentation device in position on the planar surface of the prosthesis.

2. The prosthesis system of claim 1 in which the opposed surfaces of the augmentation device are angled in respect to each other.

3. The prosthesis system of claim 1 which includes a plurality of augmentation devices, each of said devices having a different thickness.

4. The prosthesis system of claim 1 in which the cam locking mechanism includes a cam having a shaft eccentrically affixed to the cam and in which the edge of the cam is beveled to engage an undercut edge of the recess when the cam is rotated.

5. The prosthesis system of claim 4 in which a pawl is affixed to the cam and in which the distal surface of the augmentation device has a locking cavity to accept the pawl, said cavity having locking means on its edge to lock the pawl in a predetermined position when the pawl is rotated.

6. The prosthesis system of claim 5 in which the locking means comprises at least one tooth on the pawl and at least one tooth cut into the periphery of said locking cavity.

7. The prosthesis system of claim 1 in which the mechanism to secure the augmentation device includes a lug having a beveled edge adapted to engage the edge of the recess.

8. The prosthesis system of claim 1 which is a tibial component of a knee prosthesis, and in which the tibial component includes a stem on the distal surface of the component, said augmentation device further comprises an opening of a size to allow said stem to pass through said device when said device is secured to said prosthesis.

9. The prosthesis system of claim 3 in which the augmentation devices further include devices with different angles between the proximal surface and opposed distal surface.

* * * * *